United States Patent [19]

Schefczik

[11] 4,315,855
[45] Feb. 16, 1982

[54] MONOAZO DISPERSE DYES CONTAINING A NITROPHENYL GROUP AND A HOMOPHTHALIMIDE GROUP

[75] Inventor: Ernst Schefczik, Ludwigshafen, Fed. Rep. of Germany

[73] Assignee: BASF Aktiengesellschaft, Fed. Rep. of Germany

[21] Appl. No.: 707,498

[22] Filed: Jul. 22, 1976

Related U.S. Application Data

[63] Continuation of Ser. No. 188,610, Oct. 12, 1971, abandoned.

[30] Foreign Application Priority Data

Oct. 15, 1970 [DE] Fed. Rep. of Germany ....... 2050657

[51] Int. Cl.³ .................. C09B 29/42; D06P 3/26; D06P 3/42; D06P 3/54
[52] U.S. Cl. .................. 260/155; 260/326.13 D; 260/465 E; 546/142; 560/45; 562/437; 564/87; 564/441
[58] Field of Search .......................... 260/155

[56] References Cited

U.S. PATENT DOCUMENTS

| | | | |
|---|---|---|---|
| 1,893,646 | 1/1933 | Holzach et al. | 260/155 X |
| 1,969,463 | 8/1934 | Holzach et al. | 260/155 |
| 1,972,988 | 9/1934 | Giemsa et al. | 260/155 |
| 2,044,329 | 6/1936 | Raeck et al. | 260/155 |
| 2,448,871 | 9/1948 | Dickey et al. | 260/155 |
| 2,529,924 | 11/1950 | Dickey | 260/155 |
| 2,883,374 | 4/1959 | Enders | 260/155 X |
| 3,849,393 | 11/1974 | Slater et al. | 260/155 |

FOREIGN PATENT DOCUMENTS 41-16155 1/1966 Japan ........................ 260/155
46-18394 5/1971 Japan ........................ 260/155

OTHER PUBLICATIONS

Meyer et al., Compt. Rend., vol. 192, pp. 885 to 887, (1931).

*Primary Examiner*—Floyd D. Higel
*Attorney, Agent, or Firm*—Keil & Witherspoon

[57] ABSTRACT

Dyes of the formula

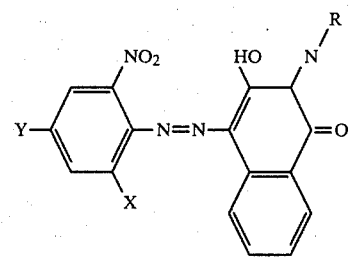

I where X and Y, for example, can be hydrogen or halogen and R can be alkyl among other substituents. The dyes are derived from an O-nitroaniline diazo component and an N-substituted homophthalimide as coupling component. The dyes are greenish yellow to orange and give clear dyeings of good color strength and having good general fastness properties on polyesters, cellulose esters and in some cases also on polyamides. The fastness to light and the fastness to heat setting are excellent and may easily be influenced by the choice of substituents.

1 Claim, No Drawings

MONOAZO DISPERSE DYES CONTAINING A NITROPHENYL GROUP AND A HOMOPHTHALIMIDE GROUP

This application is a continuation of application Ser. No. 188,610, which was filed on Oct. 12, 1971, which application has been abandoned.

The invention relates to dyes having the general formula (I):

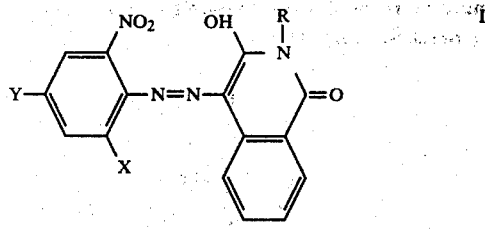

in which

X denotes hydrogen, chlorine, bromine, cyano, methylsulfonyl, carboxyl, carbalkoxy, carbamoyl or N-substituted carbamoyl;

Y denotes hydrogen, chlorine, bromine, nitro, cyano, methylsulfonyl, phenylsulfonyl, methyl, methoxy, phenylazo, carboxyl, carbalkoxy, carbamoyl, N-substituted carbamoyl, acetyl, benzoyl, sulfonamido, N-substituted sulfonamido or alkylsulfonato; and R denotes alkyl having one to eighteen carbon atoms, chloroalkyl or bromoalkyl having two or three carbon atoms, hydroxyalkyl having two to six carbon atoms, alkoxyalkyl having a total of three to eleven carbon atoms, acyloxyalkyl having three to eighteen carbon atoms, carboxyalkyl having two to six carbon atoms, carboxyalkyl having three to eleven carbon atoms, carbamoylalkyl having two to eleven carbon atoms, alkanoylaminoalkyl having three to nine carbon atoms, benzoylaminoalkyl having nine to thirteen carbon atoms, cyanoalkyl having two to six carbon atoms, polyglycol or polythioglycol radicals having four to eight carbon atoms and which may be etherified (with $C_1$ to $C_4$ alkyl) or esterified (with $C_2$ to $C_3$ alkanoyl) or radicals having the formula:

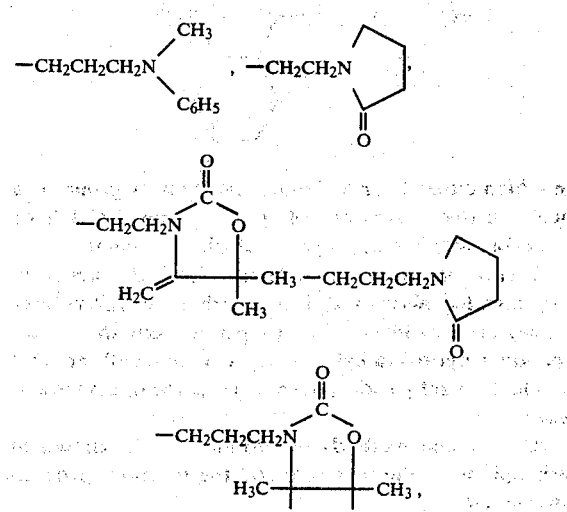

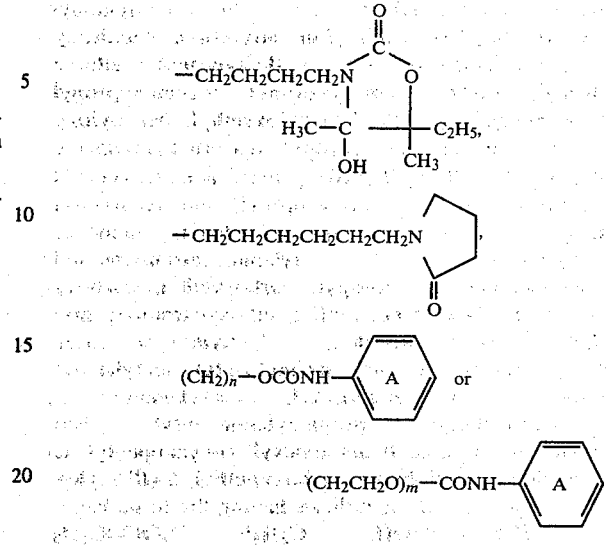

wherein the ring A may bear from one to three substituents from the series chlorine, bromine, fluorine, methyl, methoxy or trifluoromethyl;

n denotes the integer 2, 3 or 6; and m denotes the integer 2 or 3.

Examples of carbalkoxy and N-substituted carbamoyl radicals for X and Y are:

carbomethoxy, carboethoxy, carbopropoxy, carbobutoxy, carbo-$\beta$-ethylhexoxy, carbo-$\beta$-hydroxyethoxy, carbo-$\omega$-hydroxypentoxy, carbo-$\omega$-hydroxyhexoxy, carbo-$\beta$-methoxyethoxy, carbo-$\beta$-butoxyethoxy, N-methylcarbamoyl, N-ethylcarbamoyl, N-propylcarbamoyl, N-butylcarbamoyl, N-$\beta$-ethylhexylcarbamoyl, N-$\beta$-hydroxyethylcarbamoyl, N-$\beta$-hydroxypropylcarbamoyl, N-$\gamma$-hydroxypropylcarbamoyl, N-$\beta$-methoxyethylcarbamoyl, N-$\gamma$-methoxypropylcarbamoyl, N-$\gamma$-butoxypropylcarbamoyl, N-$\gamma$-($\beta'$-ethylhexoxy)-propylcarbamoyl, N,N-dimethylcarbamoyl, N,N-diethylcarbamoyl, N,N-dipropylcarbamoyl, N,N-dibutylcarbamoyl, N-methyl-N-$\beta$-hydroxyethylcarbamoyl, N,N-di-$\beta$-hydroxyethylcarbamoyl, N-benzylcarbamoyl, N-phenylethylcarbamoyl, carboxylic pyrrolidido, carboxylic piperidido and carboxylic morpholido and also the radicals having the formula:

NH—$C_2H_4OC_2H_4OH$,

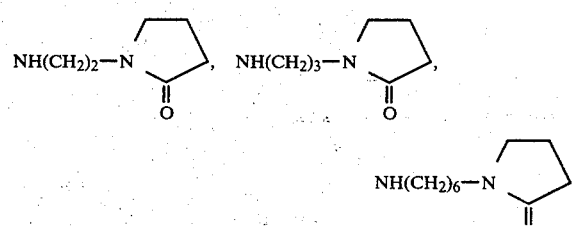

NH—$C_2H_4OC_2H_4OCH_3$ and NH—$C_2H_4OC_2H_4OC_2H_5$.

Examples of Y are the corresponding sulfonamides and suitable sulfonic alkyl esters are the alkyl esters having one to four carbon atoms, the hydroxyalkyl esters having two or three carbon atoms and the alkoxyalkyl esters having three to seven carbon atoms.

Examples of radical R are:

methyl, ethyl, propyl, isopropyl, butyl, isobutyl, tert-butyl, n-hexyl, β-ethylhexyl, n-decyl, β-methylnonyl, stearyl, β-hydroxyethyl, β-methoxyethyl, γ-hydroxypropyl, β-hydroxypropyl, γ-methoxypropyl, γ-ethoxypropyl, γ-(β-ethylhexoxy)-propyl, γ-acetoxypropyl, γ-propionyloxypropyl, benzoyloxyethyl, benzoyloxypropyl, methoxyacetoxypropyl, α-methyl-β-hydroxypropyl, β-methyl-β-hydroxypentyl, ω-hydroxyhexyl, carboxymethyl or carboxypropyl, ethoxycarbonylmethyl, methoxycarbonylpropyl, dimethylaminocarbonylmethyl, butylaminocarbonylmethyl, phenylaminocarbonylpropyl, carboxyethyl, carboxypentyl, methoxycarbonylethyl, ethoxycarbonylpentyl, diethylaminocarbonylethyl, β-ethylhexylaminocarbonylethyl, phenylaminocarbonylpentyl, acetylaminoethyl, propionylaminoethyl, acetylaminopropyl, acetylaminobutyl, propionylaminobutyl, benzoylaminobutyl, acetylaminohexyl, ω-cyanopentyl, ω-cyanohexyl, β-(β'-hydroxyethoxy)-ethyl, β-(β'-acyloxyethoxy)ethyl and the radicals having the formulae:

—C₂H₄S—C₂H₄OH, —C₂H₄S—C₂H₄OCOC₆H₅, —C₂H₄SC₂H₄OCOC₂H₅,

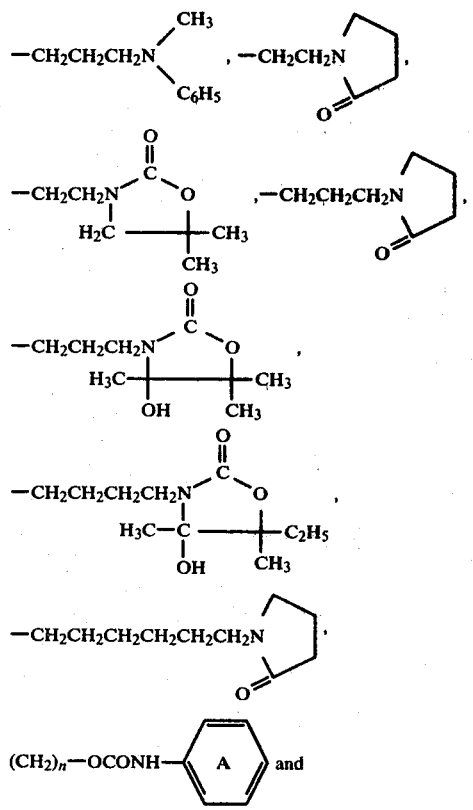

Dyes having the formula (I) are greenish yellow to orange and give clear dyeings of good color strength and having good general fastness properties on polyesters, cellulose esters and in some cases also on polyamides. The good fastness to light and the fastness to heat setting are particularly noteworthy and they may easily be influenced by the choice of substituents.

For the production of the new dyes, diazo compounds of amines having the general formula (II):

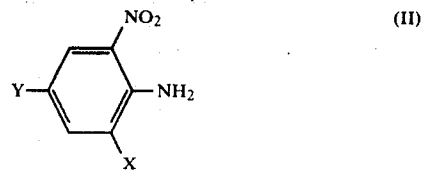

may be reacted with coupling components having the general formula (III):

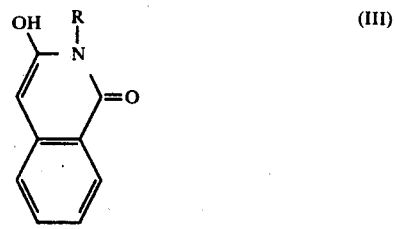

where X, Y and R have the meanings given above.

Examples of compounds having the formula (II) are: 2-nitroaniline, 2,4-dinitroaniline, 4-chloro-2-nitroaniline, 4-bromo-2-nitroaniline, 2-nitroaniline-4-carboxylic acid and its esters and amides, 4-acyl-2-nitroanilines, 2-nitroaniline-4-methylsulfone, 2-nitroaniline-4-phenylsulfone and its derivatives bearing one or more radicals such as halogen, methyl or methoxy in its phenyl radical, 2-nitroaniline-4-sulfonic esters, 2-nitroaniline-4-sulfonamide, 4-methyl-2-nitroaniline, 2-nitroaniline-6-carboxylic acid and its esters and amides, 2,4-dinitroaniline-6-carboxylic acid and its esters and amides and 4-phenylazo-2-nitroaniline.

When X or Y denotes carbalkoxy or unsubstituted or substituted carbamoyl, it may be advantageous to prepare these dyes by reaction of a compound having the formula (IV):

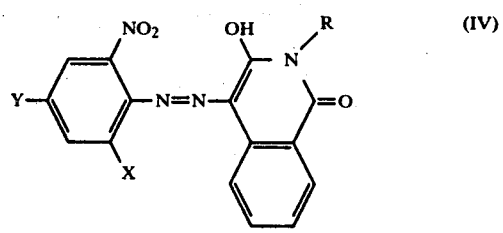

in which either X or Y denotes the COOH group or a negative derivative thereof, for example —COCl or —COBr, with the appropriate alcohol or amine.

Dyes having the formula (I) in which R denotes acyloxyalkyl, haloalkyl or arylaminocarbonyloxyalkyl (urethane) are advantageously prepared from the corresponding hydroxyalkyl dyes by reaction with an acid halide, acid anhydride, phosphorus halide or aryl isocyanate.

All the said methods of production are known in principle from the literature and the reactions proceed analogously.

Dyes having the general formula (Ia):

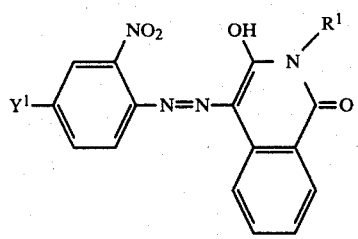

(Ia)

in which

Y[1] denotes hydrogen, chlorine, carboalkoxy or N-substituted carbamoyl; and

R[1] denotes alkyl having one to four carbon atoms, ω-hydroxyalkyl, aroyloxyalkyl, arylaminocarbonyloxyalkyl or alkanoylaminoalkyl and wherein the alkyl chain of the substituted alkyl radicals may be interrupted by oxygen atoms are of particular industrial importance.

The following Examples illustrate the invention. Parts and percentages are by weight unless stated otherwise.

EXAMPLE 1

A solution of 27.6 parts of 2-nitroaniline in 75 parts of acetic acid is poured into a mixture of 150 parts of water and 75 parts of concentrated hydrochloric acid. 200 parts of ice is added and diazotization is carried out by dripping in a solution of 15 parts of sodium nitrite in 35 parts of water. The whole is stirred for another two hours at 0° to 5° C. and excess nitrate is destroyed by adding sulfamic acid. The diazonium salt solution is stirred at 0° to 5° C. into a solution of 41 parts of N-(β-hydroxyethyl)-homophthalimide in 100 parts of water and 100 parts of dimethylformamide. The dye is precipitated as a yellow solid. It is stirred for another two hours at 0° to 5° C. and for four hours at room temperature and suction filtered, washed with water and dried.

65 parts of the dye having the constitution (R=—CH$_2$—CH$_2$—OH):

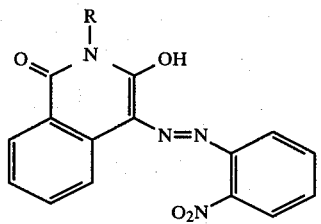

is obtained which dyes polyester and polyamide fibers and fabrics greenish yellow shades having good fastness to light and dry-heat pleating and setting.

Similar dyes are obtained from diazotized 2-nitroaniline and the substituted homophthalimides characterized by R in the following Table:

| Example | R | Shade | Material dyed |
|---|---|---|---|
| 2 | —CH$_2$CHCH$_3$<br>\|<br>CH$_3$ | greenish yellow | polyester |
| 3 | —CH$_2$CH$_2$CH$_2$OCOCH$_3$ | " | " |
| 4 | —CH$_2$CH$_2$CH$_2$NHCOC$_2$H$_5$ | " | " |
| 5 | —CH$_2$CH$_2$CH$_2$OC$_4$H$_5$ | " | " |
| 6 | —CH$_2$COOH | " | polyamide |
| 7 | —CH$_2$CONH(CH$_2$)$_3$OCH$_3$ | " | polyester |
| 8 | —CH$_2$CH$_2$CH$_2$CH$_2$CH$_2$CH$_2$OH | " | " |
| 9 | —CH$_2$CH$_2$CH$_2$CH$_2$CH$_2$CN | " | " |
| 10 | —CH$_2$CH$_2$OCH$_2$CH$_2$OH | " | " |
| 11 | —CH$_2$CH$_2$OCH$_2$CH$_2$OCOCH$_3$ | " | " |
| 12 | —CHCHOHCH$_3$<br>\|<br>CH$_3$ | " | " |
| 13 | —CH$_2$CH$_2$—N(2-pyrrolidinone) | " | " |
| 14 | —CH$_2$CH$_2$CH$_2$—N(4,4-dimethyl-5-hydroxy-oxazolidinone) | " | " |

EXAMPLE 15

A solution of 34.5 parts of 4-chloro-2-nitroaniline in 100 parts of acetic acid is poured onto a mixture of 150 parts of concentrated hydrochloric acid and 150 parts of ice. Then, while stirring, a solution of 15 parts of sodium nitrite in 35 parts of water is run in and diazotization is completed by stirring for another four hours at 0° to 5° C. After excess nitrite has been destroyed, the diazonium salt solution is introduced in portions while stirring into a solution of 43.8 parts of N-(γ-hydroxypropyl)-homophthalimide in 40 parts of acetic acid and 240 parts of water which is kept at +5° C. Stirring is continued for another four hours at 5° to 10° C. and the dye suction filtered, washed with water and dried. 76 parts of the dye having the formula (R=—CH$_2$—CH$_2$—CH$_2$—OH):

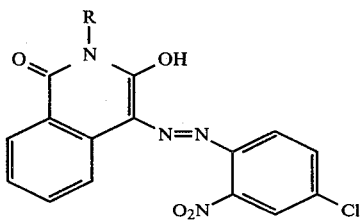

is obtained in the form of an orange powder. It dyes fibers and fabrics of polyesters full, neutral yellow shades having excellent fastness to light and dry-heat pleating and setting.

Other Examples of dyes having Y denoting Cl in formula (I) are:

| Example | R | Shade | Materials dyed |
|---|---|---|---|
| 16 | —CH$_3$ | yellow | polyester |
| 17 | —CH$_2$CHCH$_2$CH$_2$CH$_2$CH$_3$ <br> \| <br> C$_2$H$_5$ | " | " |
| 18 | —(CH$_2$)$_{17}$CH$_3$ | " | " |
| 19 | —CH$_2$CH$_2$OH | " | " |
| 20 | —CH$_2$CHOHCH$_3$ | " | " |
| 21 | —CH$_2$—COH—C$_3$H$_7$ <br> \| <br> CH$_3$ | " | " |
| 22 | —CH$_2$CH$_2$OCOC$_2$H$_5$ | " | " |
| 23 | —CH$_2$CH$_2$OCH$_2$CH$_2$OH | " | " |
| 24 | —CH$_2$CH$_2$CH$_2$OCOC$_2$H$_5$ | " | " |
| 25 | —CH$_2$CH$_2$CH$_2$OC$_2$H$_5$ | " | " |
| 26 | —CH$_2$CON(C$_2$H$_5$)$_2$ | " | " |
| 27 | —CH$_2$CON(CH$_2$CH$_2$OH)$_2$ | " | " |
| 28 | —CH$_2$CH$_2$COOH | " | polyamide |
| 29 | —CH$_2$CH$_2$NHCOCH$_3$ | " | polyester |
| 30 | —CH$_2$CH$_2$CH$_2$CH$_2$NHCOCH$_3$ | " | " |
| 31 | —CH$_2$CH$_2$CH$_2$CH$_2$CH$_2$CH$_2$CN | " | " |
| 32 | —CH$_2$CH$_2$CH$_2$N(CH$_3$)(C$_6$H$_5$) | " | " |
| 33 | —CH$_2$CH$_2$CH$_2$N(pyrrolidinone) | " | " |
| 34 | —CH$_2$CH$_2$CH$_2$CH$_2$CH$_2$CH$_2$N(pyrrolidinone) | " | " |
| 35 | —CH$_2$CH$_2$N(oxazolidinone-dimethyl) | " | " |

EXAMPLE 36

30.4 parts of 4-methyl-2-nitroaniline is dissolved in a mixture of 50 parts of acetic acid, 75 parts of concentrated hydrochloric acid and 150 parts of water. Diazotization is carried out by dripping in a solution of 15 parts of sodium nitrite in 35 parts of water at 0° to 5° C. and stirring for another two hours at this temperature. Excess nitrite is destroyed with sulfamic acid and the diazonium salt solution is dripped into a solution of 49.4 parts of N-(β-acetoxyethyl)-homophthalimide in 100 parts of acetic acid and 100 parts of water. The temperature is kept at about +5° C. by adding ice. The whole is stirred for another four hours at about +5° C. and for another sixteen hours at room temperature and then the dye is suction filtered, washed with water and dried. 73 parts of the dye having the formula (R=CH$_2$—CH$_2$OCOCH$_3$):

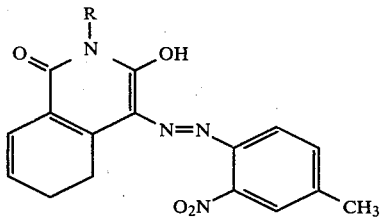

is obtained in the form of a reddish yellow powder.

Reddish yellow dyeings having good fastness to light and dry-heat pleating and setting are obtained therewith on polyesters.

The following dyes are obtained with the same diazo component with other substituted homophthalimides:

| Example | R | Shade | Material dyed |
|---|---|---|---|
| 37 | —CH$_2$CH$_3$ | reddish yellow | polyester |
| 38 | —CH$_2$CH$_2$CH$_2$CH$_3$ | " | " |
| 39 | —CH$_2$CH$_2$OH | " | polyamide |
| 40 | —CH$_2$CH$_2$CH$_2$OH | " | polyester |
| 41 | —CH$_2$CH$_2$CH$_2$OCH$_3$ | " | " |
| 42 | —CH$_2$CON(cyclohexyl) | " | " |
| 43 | —CH$_2$CH$_2$CH$_2$COOC$_2$H$_5$ | " | " |
| 44 | —CH$_2$CH$_2$OCH$_2$CH$_2$OH | " | " |
| 45 | —CH$_2$CH$_2$NHCOC$_2$H$_5$ | " | " |

EXAMPLE 46

36.6 parts of 2,4-dinitroaniline is introduced at 5° to 10° C. into a solution of 15 parts of sodium nitrite in 350 parts of 85% sulfuric acid. After stirring for four hours at this temperature, the sulfuric acid solution is poured onto 1000 parts of ice and the excess nitrite is destroyed with sulfamic acid. Then a solution of 35 parts of N-methylhomophthalimide in 250 parts of dimethylformamide is dripped in and the acid is neutralized by adding 150 parts of 25% ammonia solution in portions. The whole is stirred for another two hours at 10° C. and for sixteen hours at room temperature, suction filtered, washed with water and dried. 65 parts of the dye having the formula (R=CH$_3$):

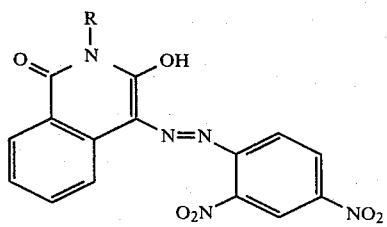

is obtained. Neutral yellow dyeings having good light fastness and thermal stability are obtained with the dye on polyesters.

The following dyes are obtained analogously with the same diazo component:

| Example | R | Shade | Material dyed |
|---|---|---|---|
| 47 | —CH₂CH₂CH₃ | yellow | polyester |
| 48 | —(CH₂)₉CH₃ | " | " |
| 49 | —CH₂CH₂OCOCH₃ | " | " |
| 50 | —CH₂CH₂CH₂OH | " | " |
| 51 | —CH₂CONHCH₂CH(CH₂)₃CH₃ <br>                                \|<br>                               C₂H₅ | " | " |
| 52 | —CH₂CH₂CH₂CH₂CH₂CH₂NHCOCH₃ | " | " |
| 53 | —CH₂CH₂CH₂N⟨pyrrolidinone⟩ | | |
| 54 | —CH₂CH₂CH₂CH₂N-carbamate structure with HO, CH₃, CH₃, CH₃ | " | " |

EXAMPLE 55

The 2,4-dinitroaniline in Example 46 is replaced by 47.6 parts of the butyl ester of 2-nitroaniline-4-carboxylic acid and otherwise the procedure of Example 46 is adopted. 76 parts of a yellow dye having the formula:

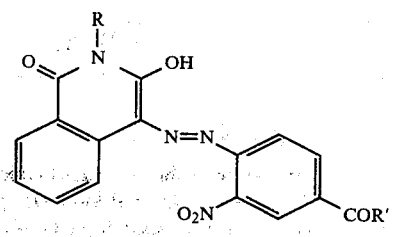

(R=CH₃; R'=OC₄H₉) is obtained which gives greenish yellow dyeings having very good fastness to light and dry-heat pleating and setting on polyesters.

The following dyes are prepared analogously:

| Example | R | R' | Shade | Material dyed |
|---|---|---|---|---|
| 56 | —CH₃ | —OCH₂CH₂OH | greenish yellow | polyester |
| 57 | —CH₃ | —OCH₂CH(CH₂)₃CH₃<br>           \|<br>           C₂H₅ | " | " |
| 58 | —CH₃ | —OCH₂CH₂CH₂CH₂OH | " | " |
| 59 | —CH₃ | —NHC₃H₉ | " | " |
| 60 | —CH₃ | —NHCH₂CH(CH₂)₃CH₃<br>            \|<br>            C₂H₅ | " | " |
| 61 | —CH₃ | —NHCH₂CH₂CH₂OC₂H₅ | " | " |
| 62 | —CH₃ | —NHCH₂CH₂C₆H₅ | " | " |
| 63 | —CH₃ | —N(C₄H₉)₂ | " | " |
| 64 | —CH₃ | —N⟨pyrrolidine⟩ | | |
| 65 | —CH₃ | —NHCH₂CH₂OCH₂CH₂OH | " | " |
| 66 | —CH₃ | —NH(CH₂)₆N⟨pyrrolidinone⟩ | | |
| 67 | —C₂H₅ | —OC₂H₅ | " | " |
| 68 | —C₂H₅ | —NHC₂H₅ | " | " |
| 69 | —CH₂CH₂OH | —OC₄H₉ | " | " |
| 70 | —CH₂CH₂CH₂OH | —OC₂H₅ | " | " |
| 71 | —CH₂COOH | —OC₂H₅ | yellow | polyamide |
| 72 | —CH₂CH₂CH₂OCH₃ | —OC₄H₉ | greenish yellow | polyester |
| 73 | —CH₂CH₂OCH₂CH₂OH | —OC₂H₅ | " | " |
| 74 | —CH₂CH₂N⟨pyrrolidinone⟩ | —OC₄H₉ | " | " |
| 75 | —CH₂CH₂OH | —CH₃ | yellow | " |
| 76 | —CH₂CH₂CH₂OC₂H₅ | —CH₃ | " | " |
| 77 | —C₄H₉ | —C₆H₅ | " | " |
| 78 | —CH₂CH₂OCH₂CH₂OH | —C₆H₅ | " | " |
| 79 | —(CH₂)₆OH | —C₆H₅ | " | " |

-continued

| Example | R | R' | Shade | Material dyed |
|---|---|---|---|---|
| 80 | —(CH$_2$)$_5$CN | —C$_6$H$_5$ | " | " |
| 81 | —CH$_2$CH(CH$_2$)$_3$CH$_3$<br>\|<br>C$_2$H$_5$ | —⟨○⟩—Cl | " | " |
| 82 | —(CH$_2$)$_4$NHCOCH$_3$ | —⟨○⟩—CH | " | " |

EXAMPLE 83

36.4 parts of 3-nitro-4-aminobenzoic acid is dissolved in 300 parts of 3% caustic soda solution. 15 parts of sodium nitrite, 250 parts of ice and 80 parts of concentrated hydrochloric acid are added to the solution in this sequence and the whole is stirred for another four hours at 0° to 5° C. Excess nitrite is then destroyed and the diazonium salt solution is dripped into a solution of 41 parts of N-(β-hydroxyethyl)-homophthalimide in 250 parts of 25% acetic acid. The acid is then neutralized by batchwise addition of 75 parts of concentrated ammonia solution. The whole is stirred for two hours at 5° C. and for sixteen hours at room temperature, suction filtered, washed with water and dried. 77 parts of the dye having the formula (R=—CH$_2$—CH$_2$—OH):

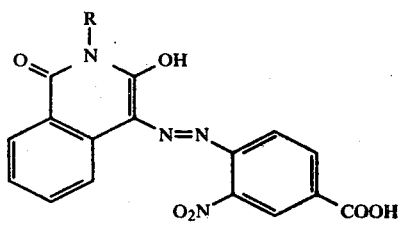

is obtained in the form of a brown powder.

The dye gives yellow shades on polyamide fibers and cloth when applied from an aqueous liquor; the dyeings have good fastness to light and dry-heat pleating and setting.

Dyes having similar tinctorial properties are obtained when the homophthalimides characterized by R in the following Table are used as coupling components:

| Example | R | Shade | Material dyed |
|---|---|---|---|
| 84 | —CH$_3$ | yellow | polyamide |
| 85 | —CH$_2$CH$_2$CH$_2$CH$_2$CH$_3$ | " | " |
| 86 | —CH$_2$CH$_2$CH$_2$OH | " | " |
| 87 | —CH$_2$CH$_2$CH$_2$OC$_2$H$_5$ | " | " |
| 88 | —CH$_2$CH$_2$OCOCH$_3$ | " | " |
| 89 | —CH$_2$CH$_2$OCH$_2$CH$_2$OH | " | " |

-continued

| Example | R | Shade | Material dyed |
|---|---|---|---|
| 90 | —CH$_2$CH$_2$N⟨(CH$_2$)$_3$C=O⟩ | " | " |
| 91 | —CH$_2$COOH | " | " |
| 92 | —CH$_2$CH$_2$COOH | " | " |
| 93 | —CH$_2$CH$_2$CH$_2$CH$_2$CH$_2$COOH | " | " |

EXAMPLE 94

42.0 parts of ethyl 2-amino-3-nitrobenzoate is introduced at 0° to 5° C. into a solution of 15 parts of sodium nitrite in 400 parts of 85% sulfuric acid. The whole is stirred for four hours at 5° C. The diazonium solution is poured onto 1500 parts of ice and the excess nitrite is destroyed by adding sulfamic acid. A solution of 41.0 parts of N-(β-hydroxyethyl)-homophthalimide in 100 parts of dimethylformamide and 100 parts of water is then dripped in while stirring and cooling with ice. The acid is gradually neutralized with aqueous ammonia. The whole is stirred for another two hours at 5° C. and for twelve hours at room temperature, suction filtered, washed with water and dried. 77 parts of the dye having the formula (R=—CH$_2$—CH$_2$—OH; R'=—OC$_2$H$_5$):

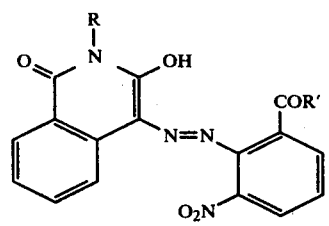

The dye gives greenish yellow dyeings having good fastness to light and dry-heat pleating and setting on polyesters.

The dyes set out in the following Table are obtained analogously:

| Example | R | R' | Shade | Material dyed |
|---|---|---|---|---|
| 95 | —CH$_3$ | —OCH$_2$CH(C$_2$H$_5$)—(CH$_2$)$_3$CH$_3$ | greenish yellow | polyester |
| 96 | —CH$_2$CH$_2$CH$_2$OH | —OC$_4$H$_9$ | " | " |
| 97 | —CH$_2$CH$_2$CH$_2$OH | —NHC$_4$H$_9$ | " | " |
| 98 | " | —NHCH$_2$CH$_2$CH$_2$OC$_2$H$_5$ | " | " |
| 99 | " | —N(CH$_3$)$_2$ | " | " |
| 100 | " | —N⟨CH$_3$ / CH$_2$CH$_2$OH⟩ | " | " |
| 101 | —CH$_2$CH$_2$OCH$_2$CH$_2$OH | —OC$_2$H$_5$ | " | " |
| 102 | " | —N(C$_2$H$_5$)$_2$ | " | " |

-continued

| Example | R | R' | Shade | Material dyed |
|---|---|---|---|---|
| 103 | " | —C$_6$H$_4$CH$_3$(p) | " | " |
| 104 | —CH$_2$CH$_2$OH | —OH | " | polyamide |
| 105 | —CH$_2$CH$_2$CH$_2$OH | —OH | " | " |
| 106 | —CH$_2$CH$_2$OCH$_2$CH$_2$OH | —OH | " | " |
| 107 | —CH$_2$COOH | —OH | " | " |
| 108 | —CH$_2$CH$_2$COOH | —OH | " | " |
| 109 | —(CH$_2$)$_5$COOH | —OH | " | " |

EXAMPLE 110

The ethyl 2-amino-3-nitrobenzoate of Example 94 is replaced by 51 parts of ethyl 2-amino-3,5-dinitrobenzoate. 86.4 parts of the dye having the formula (R=—CH$_2$—CH$_2$—OH; R'=—C$_2$H$_5$):

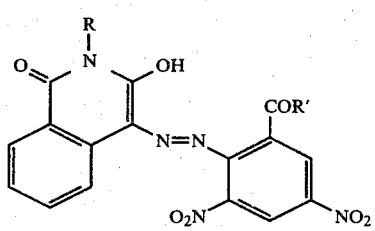

is obtained. It dyes fibers and cloth of polyesters greenish yellow shades having good fastness to light and dry-heat pleating and setting.

The following dyes are obtained analogously to Example 110:

C. The mixture is then poured onto 1200 parts of ice and a little sulfamic acid. A solution of 46.6 parts of N-(γ-methoxypropyl)-homophthalimide in 400 parts of 50% acetic acid is then dripped in. Coupling is completed by neutralization to pH about 5 with aqueous ammonia solution and the whole is stirred for some hours, suction filtered, washed with water and dried. 89 parts of the dye having the formula (R=—CH$_2$—CH$_2$—CH$_2$—OCH$_3$; R'=—NHCH$_3$):

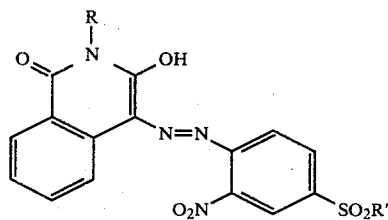

is obtained. Greenish yellow dyeings which are distinguished by very good fastness to light and thermal sta-

| Example | R | R' | Shade | Material dyed |
|---|---|---|---|---|
| 111 | —CH$_2$CH$_2$CH$_2$OC$_2$H$_5$ | —OC$_2$H$_5$ | greenish yellow | polyester |
| 112 | —CH$_2$CH$_2$OH | —OC$_4$H$_9$ | greenish yellow | " |
| 113 | —(CH$_2$)$_6$OH | —OC$_4$H$_9$ | greenish yellow | " |
| 114 | —CH$_2$CH$_2$CH$_2$OH | —NHCH$_2$CH$_2$—CH$_2$OCH$_3$ | greenish yellow | " |
| 115 | —CH$_2$CH$_2$CH$_2$OH | —N(C$_4$H$_9$)$_2$ | greenish yellow | " |
| 116 | —CH$_2$CH$_2$OH | —NHCH$_2$CH$_2$CH$_2$OH | greenish yellow | " |
| 117 | —CH$_2$CH$_2$OCH$_2$CH$_2$OH | —NHCH$_3$ | greenish yellow | " |
| 118 | —CH$_2$CH$_2$OCH$_2$CH$_2$OH | —N(CH$_3$)$_2$ | greenish yellow | " |

EXAMPLE 119

46.2 parts of 2-nitroaniline-4-sulfonic-N-methylamide is introduced into 300 parts of nitrosylsulfuric acid (equivalent to 15 parts of sodium nitrite) while cooling with ice. The whole is stirred for four hours at 0° to 5° bility are obtained with the dye on polyester threads, filaments and cloth from an aqueous liquor.

The following dyes are obtained by varying the radicals R and R' in the diazo component and coupling component:

| Example | R | R' | Shade | Material dyed |
|---|---|---|---|---|
| 120 | —CH$_3$ | —NHCH$_2$CH(C$_2$H$_5$)(CH$_2$)$_3$CH$_3$ | greenish yellow | polyester |
| 121 | —CH$_3$ | —N(C$_4$H$_9$)$_2$ | " | " |
| 122 | —CH$_2$CH$_2$OH | —NHCH$_3$ | " | " |
| 123 | —CH$_2$CH$_2$CH$_2$OH |  | " | " |

| Example | R | R' | Shade | Material dyed |
|---|---|---|---|---|
| 124 | —CH₂CH₂OCH₂CH₂OH | —N(morpholino) | " | " |
| 125 | —CH₂CH₂CH₂OCH₃ | —OC₄H₉ | " | " |
| 126 | —(CH₂)₉CH₃ | —CH₃ | " | " |
| 127 | —CH₂CH₂OH | —CH₃ | " | " |
| 128 | —CH—CHOH—CH₃ (with CH₃) | —CH₃ | " | " |
| 129 | —CH₂C(CH₃)(OH)—CH₂CH₂CH₃ | —CH₃ | " | " |
| 130 | —CH₂CH₂CH₂CH₂NHCOC₂H₅ | —CH₃ | " | " |
| 131 | —CH₂CHOHCH₃ | —C₆H₅ | " | " |
| 132 | —CH₂CH(C₂H₅)CH₂CH₂CH₂CH₃ | —C₆H₅ | " | " |
| 133 | —CH₂CH₂OH | —C₆H₄—CH₃(p) | " | " |
| 134 | —CH₂CH₂OCH₂CH₂OH | —C₆H₄OCH₃(p) | " | " |
| 135 | —(CH₂)₆OH | —C₆H₄Cl(p) | " | " |

EXAMPLE 136

48.4 parts of 3-nitro-4-aminoazobenzene is dissolved in 300 parts of warm glacial acetic acid and the solution is poured onto a mixture of 100 parts of concentrated hydrochloric acid and 400 parts of ice. Diazotization is then carried out by dripping in a solution of 15 parts of sodium nitrite in 30 parts of water and stirring for another four hours at 0° to 5° C. Excess nitrite is then destroyed with sulfamic acid and the diazonium salt solution is dripped while cooling into a solution of 35.0 parts of N-methylhomophthalimide in 150 parts of dimethylformamide and 150 parts of 20% acetic acid. The temperature is kept at 0° to 5° C. for another two hours by adding ice and neutralization with aqueous ammonia is carried out at the same time. After another sixteen hours at room temperature, the dye is suction filtered, washed with water and dried. 80.7 parts of the dye having the formula (R=—CH₃):

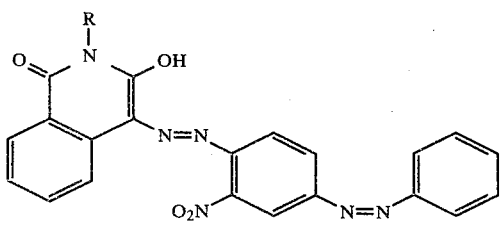

is obtained in the form of a brown powder.

The dye gives golden yellow shades having good color strength and very good fastness to light and dry-heat pleating and setting on polyester material.

The following dyes are obtained analogously:

| Example | R | Shade | Material dyed |
|---|---|---|---|
| 137 | —C₂H₅ | golden yellow | polyester |
| 138 | —CH₂CH₂OH | " | " |
| 139 | —CH₂CH₂CH₂OH | " | " |
| 140 | —CH₂CH₂CH₂OCH₃ | " | " |
| 141 | —CH₂CH₂CH₂OCOCH₃ | " | " |

EXAMPLE 142

A mixture of 200 parts of hexanediol-(1,6), 20 parts of p-toluenesulfonic acid and 36.8 parts of the dye from Example 84 is stirred for eight hours at 130° C. After cooling, the whole is diluted with 300 parts of methanol and the precipitate is suction filtered, washed with methanol and dried. 41 parts of a dye having the formula:

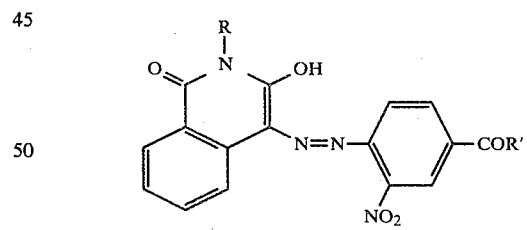

(R=CH₃; R'=—O(CH₂)₆OH) is obtained. It gives greenish yellow dyeings having very good fastness to light and dry-heat pleating and setting on polyesters.

The following dyes are prepared analogously:

| Example | R | R' | Shade | Material dyed |
|---|---|---|---|---|
| 143 | —CH₃ | —O(CH₂)₄CH₃ | greenish yellow | polyester |
| 144 | —CH | —OCH₂CH(C₂H₅)(CH₂)₃CH₃ | " | " |
| 145 | —C₂H₅ | —O(CH₂)₅OH | " | " |
| 146 | —C₂H₅ | —OCH₂CH₂OCH₂CH₂OCH₃ | " | " |
| 147 | —C₄H₉ | —O(CH₂)₂OH | " | " |
| 148 | —C₄H₉ | —O(CH₂)₄OH | " | " |

-continued

| Example | R | R' | Shade | Material dyed |
|---|---|---|---|---|
| 149 | —(CH$_2$)$_3$OCH$_3$ | —O(CH$_2$)$_3$CH$_3$ | " | " |
| 150 | —(CH$_2$)$_3$OCH$_3$ | —O(CH$_2$)$_2$OH | " | " |
| 151 | —(CH$_2$)$_3$OCH$_3$ | —O(CH$_2$)$_2$OCH$_3$ | " | " |

EXAMPLE 152

36.8 parts of the dye of Example 84 is suspended in 375 parts of chlorobenzene and after 1 part of dimethylformamide and 15 parts of thionyl chloride have been added the whole is stirred for eight hours on a boiling waterbath. After cooling, the precipitate is suction filtered, washed with benzene and dried. 34.8 parts of the corresponding acid chloride (R=CH$_3$; R'=Cl) is obtained in the form of yellow crystals having a melting point of 272° C. to 273° C. (with decomposition) and a chlorine content of 9.5% (calculated: 9.1%).

200 parts of pentanediol-(1,5), 10 parts of pyridine and 38.65 parts of the acid chloride thus obtained are stirred for two hours at 100° to 120° C. After cooling, the whole is diluted with 300 parts of methanol and the precipitate is suction filtered, washed with methanol and dried. 40.1 parts of the dye having the formula (see Example 142) (R=CH$_3$; R'=—O(CH$_2$)$_5$OH) is obtained. It dyes fibers and cloth of polyesters greenish yellow shades having excellent fastness to light and dry-heat pleating and setting.

EXAMPLE 153

38.65 parts of the acid chloride prepared according to Example 152 is introduced into 200 parts of dimethylformamide, 17 parts of pyrrolidine is added and the whole is stirred for two hours at 120° C., diluted with 100 parts of 50% aqueous methanol, allowed to cool, suction filtered, washed with water and dried. 40.1 parts of a dye is obtained which is identical chemically and tinctorially with the dye obtained according to Example 64.

EXAMPLE 154

A mixture of 350 parts of chlorobenzene, 15 parts of thionyl chloride, 1 part of dimethylformamide and 42.4 parts of the dye from Example 85 is kept at 95° to 100° C. for six hours. 50 parts is distilled off at a pressure of about 50 mm so that excess thionyl chloride is removed. A weak current of gaseous dimethylamine is passed into the remaining solution of the acid chloride at 100° C. for about two hours and then the reaction mixture is subjected to steam distillation. The dye which after this is present as an aqueous suspension is suction filtered, washed with water and dried at 50° C. at subatmospheric pressure. 39 parts of a compound (R=—C$_5$H$_{11}$;

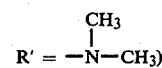

is obtained which exhibits tinctorial properties on polyesters which are similar to those of the dye of Example 153.

Dyes having the formula according to Example 142 which are characterized in the following Table by R and R' are obtained analogously to the procedure described in Examples 152 to 154:

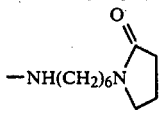

-continued

| Example | R | R' | Shade | Material dyed |
|---|---|---|---|---|
| 176 | " | —NH(CH₂)₃N(C₄H₉)(C₆H₅) | " | " |
| 177 | " | —N(CH₃)₂ | " | " |
| 180 | " | —N(C₂H₅)₂ | " | " |
| 181 | " | —N(C₃H₇)₂ | " | " |
| 182 | " | —N(C₄H₉)₂ | " | " |
| 183 | " | —N(CH₃)(CH₂CH₂OH) | " | " |
| 184 | " | —N(C₆H₅)(CH₂CH₂CN) | " | " |
| 185 | —CH₃ | —N(C₆H₅)(CH₂CH₂OH) | " | " |
| 186 | " | —N(pyrrolidine) | " | " |
| 187 | " | —N(piperidine) | " | " |
| 188 | " | —N(morpholine) | " | " |
| 189 | —C₂H₅ | —OC₂H₅ | " | " |
| 190 | " | —OCH₂CH₂OH | " | " |
| 191 | " | —OCH₂CH₂OCH₂CH₂OH | " | " |
| 192 | " | —N(C₄H₉)₂ | " | " |
| 193 | " | —NH(CH₂)₃OC₂H₅ | " | " |
| 194 | " | —NH(CH₂)₅CN | " | " |
| 195 | " | —NH(CH₂)₃N(2-pyrrolidinone) | " | " |
| 196 | " | —NHCH₂CH₂C₆H₅ | " | " |
| 197 | —C₄H₉ | —OCH₃ | " | " |
| 198 | " | —OCH₂CH₂CH₂CH₂OH | " | " |
| 199 | " | —OCH₂CH₂OCH₂CH₂OH | " | " |
| 200 | " | —NHCH₃ | " | " |
| 201 | " | —NHCH₂CH₂CH₂OCH₃ | " | " |
| 202 | " | —NHCH₂C₆H₅ | " | " |
| 203 | " | —N(CH₃)₂ | " | " |
| 204 | " | —N(piperidine) | " | " |
| 205 | " | —N(morpholine) | " | " |
| 206 | —CH₂CH₂CH₂OCH₃ | —OC₂H₅ | " | " |
| 207 | " | —OCH₂CH₂OH | " | " |
| 208 | " | —O(CH₂)₅OH | " | " |
| 209 | " | —NHCH₂CH₂OH | " | " |
| 210 | " | —NH(CH₂)₂N(2-pyrrolidinone) | " | " |
| 211 | " | —N(CH₃)₂ | " | " |
| 212 | —CH₂CH₂CH₂OCH₃ | —N(CH₂CH₂OH)₂ | " | " |
| 213 | " | —N(CH₃)(C₆H₅) | " | " |

| Example | R | R' | Shade | Material dyed |
|---------|---|----|----|----|
| 214 | " | —NH(CH$_2$)$_3$N(CH$_3$)(C$_6$H$_5$) | " | " |
| 215 | " | 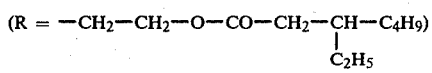 | " | " |

EXAMPLE 216

35.4 parts of the dye from Example 1 and 30 parts of 2-ethylhexanoic acid anhydride are introduced into 250 parts of pyridine. The whole is boiled under reflux for one hour and then poured onto ice and excess hydrochloric acid. The deposited dye is suction filtered, washed with dilute hydrochloric acid and with water and dried. 44.5 parts of dye (R = —CH$_2$—CH$_2$—O—CO—CH$_2$—CH(C$_2$H$_5$)—C$_4$H$_9$)

is obtained which gives clear greenish yellow dyeings having good fastness to light and dry-heat pleating and setting on polyesters.

EXAMPLE 217

A mixture of 200 parts of dimethylformamide, 40.25 parts of the dye from Example 15, 15.11 parts of triethylamine and 14.5 parts of benzoyl chloride is stirred for two hours at 120° C. The whole is then poured onto ice and worked up as described in Example 216. 49 parts of the corresponding dye with R=—CH$_2$—CH$_2$—CH$_2$—O—CO—C$_6$H$_5$ is obtained which dyes polyester material yellow shades. The dyeings have excellent fastness to light and dry-heat pleating and setting.

The dyes characterized in the following Table by their substituents are obtained analogously to the specified procedure:

| Example | R | Shade | Material dyed |
|---------|---|-------|---------------|
| Formula (I): X = Y = H | | | |
| 218 | —(CH$_2$)$_2$OCOCH$_3$ | greenish yellow | polyester |
| 219 | —(CH$_2$)$_2$OCOCH$_2$OCH$_3$ | " | " |
| 220 | —(CH$_2$)$_2$OCOC(CH$_3$)$_3$ | " | " |
| 221 | —(CH$_2$)$_2$OCOC$_4$H$_9$ | " | " |
| 222 | —(CH$_2$)$_2$OCOC$_6$H$_5$ | " | " |
| 223 | —(CH$_2$)$_2$OCOCH$_2$C$_6$H$_5$ | " | " |
| 224 | —(CH$_2$)$_2$OCO—C$_6$H$_4$—Cl | " | " |
| 225 | —(CH$_2$)$_2$OCO—C$_6$H$_3$(Cl)—Cl | " | " |
| 226 | —(CH$_2$)$_2$OCO—C$_6$H$_4$—NO$_2$ | " | " |
| 227 | —(CH$_2$)$_2$OCO—C$_6$H$_4$—COOH | " | " |
| 228 | —(CH$_2$)$_3$OCOCH$_2$CH$_2$CH$_3$ | " | " |
| 229 | —(CH$_2$)$_3$OCOCH$_2$OCH$_3$ | " | " |
| 230 | —(CH$_2$)$_3$OCOCH$_2$CH$_2$COOH | " | " |
| 231 | —(CH$_2$)$_3$OCO—C$_6$H$_4$—Cl | " | " |
| 232 | —(CH$_2$)$_3$OCO—C$_6$H$_3$(Cl)—Cl | " | " |
| 233 | —(CH$_2$)$_3$OCO—C$_6$H$_4$—NO$_2$ | " | " |
| 234 | —(CH$_2$)$_3$OCO—C$_6$H$_4$—OCH$_3$ | " | " |
| 235 | —(CH$_2$)$_6$OCOC$_6$H$_5$ | " | " |
| 236 | —(CH$_2$)$_6$OCO—C$_6$H$_4$—Cl | " | " |

-continued

| Example | R | Shade | Material dyed |
|---|---|---|---|
| 237 | —(CH$_2$)$_6$OCO—C$_6$H$_3$(HOOC)—H | " | " |
| 238 | —(CH$_2$)$_2$O(CH$_2$)$_2$OCOCCl$_3$ | " | " |
| 239 | —(CH$_2$)$_2$O(CH$_2$)$_2$OCOC$_6$H$_5$ | " | " |
| 240 | —(CH$_2$)$_2$O(CH$_2$)$_2$OCO—C$_6$H$_3$Cl$_2$ | " | " |
| 241 | —(CH$_2$)$_2$O(CH$_2$)$_2$OCO—C$_6$H$_4$(HOOC) | " | " |
| 242 | —(CH$_2$)$_2$O(CH$_2$)$_2$OCO—C$_6$H$_3$(NO$_2$)(Cl) | " | " |
| Formula (I): X = H  Y = Cl | | | |
| 243 | —(CH$_2$)$_2$OCOCH$_2$CH$_3$ | yellow | " |
| 244 | —(CH$_2$)$_2$OCOCH$_2$OCH$_3$ | " | " |
| 245 | —(CH$_2$)$_3$OCOCHCl$_3$ | " | " |
| 246 | —(CH$_2$)$_2$OCOCH$_2$CH$_2$COOH | " | " |
| 247 | —(CH$_2$)$_2$OCOCH$_2$CH(C$_3$H$_5$)CH$_2$CH$_2$CH$_3$ | " | " |
| 248 | —(CH$_2$)$_2$OCO—C$_6$H$_4$—Cl | " | " |
| 249 | —(CH$_2$)$_2$OCO—C$_6$H$_3$Cl$_2$ | " | " |
| 250 | —(CH$_2$)$_2$OCO—C$_6$H$_4$—CH$_3$ | " | " |
| 251 | —(CH$_2$)$_2$—OCO—C$_6$H$_4$—OCH$_3$ | " | " |
| 252 | —(CH$_2$)$_2$OCO—C$_6$H$_4$—NO$_2$ | " | " |
| 253 | —(CH$_2$)$_2$OCO—C$_6$H$_4$—COOH | " | " |
| 254 | —(CH$_2$)$_2$OCO—C$_6$H$_3$(CH$_3$)—CO—N(CH$_2$CH$_2$CH$_2$OCH$_3$)—CO— | " | " |
| 255 | —(CH$_2$)$_3$OCOC(CH$_3$)$_3$ | " | " |
| 256 | —(CH$_2$)$_3$OCOCH$_2$CH(C$_2$H$_5$)CH$_2$CH$_2$CH$_3$ | " | " |
| 257 | —(CH$_2$)$_3$OCOCCl$_3$ | " | " |
| 258 | —(CH$_2$)$_3$OCO—C$_6$H$_4$—Cl | " | " |
| 259 | —(CH$_2$)$_3$OCO—C$_6$H$_3$Cl$_2$ | " | " |
| 260 | —(CH$_2$)$_3$OCO—C$_6$H$_3$Cl$_2$ | " | " |
| 261 | —(CH$_2$)$_3$OCO—C$_6$H$_4$—NO$_2$ | " | " |
| 262 | —(CH$_2$)$_3$OCO—C$_6$H$_3$(NO$_2$)(Cl) | " | " |

-continued

| Example | R | Shade | Material dyed |
|---|---|---|---|
| 263 | —(CH$_2$)$_3$OCO—C$_6$H$_4$(HOOC) | " | " |
| 264 | —(CH$_2$)$_6$OCOC$_6$H$_5$ | " | " |
| 265 | —(CH$_2$)$_6$OCO—C$_6$H$_4$—Cl | " | " |
| 266 | —(CH$_2$)$_6$OCO—C$_6$H$_4$—NO$_2$ | " | " |
| 267 | —(CH$_2$)$_2$O(CH$_2$)$_2$OCOCH$_2$OCH$_3$ | " | " |
| 268 | —(CH$_2$)$_2$O(CH$_2$)$_2$OCOCCl$_3$ | " | " |
| 269 | —(CH$_2$)$_2$O(CH$_2$)$_2$OCOC$_6$H$_5$ | " | " |
| 270 | —(CH$_2$)$_2$O(CH$_2$)$_2$OCO—C$_6$H$_4$—Cl | " | " |
| 271 | —(CH$_2$)$_2$O(CH$_2$)$_2$OCO—C$_6$H$_3$(NO$_2$)—Cl | " | " |
| 272 | —(CH$_2$)$_2$O(CH$_2$)$_2$OCO—C$_6$H$_3$(HOOC)—Cl | " | " |

Formula (I): X = H  Y = CH$_3$

| | | | |
|---|---|---|---|
| 273 | —(CH$_2$)$_3$OCO(CH$_3$)$_3$ | reddish yellow | " |
| 274 | —(CH$_2$)$_3$OCOCH$_2$CH$_2$COOH | " | " |
| 275 | —(CH$_2$)$_3$OCOC$_6$H$_5$ | " | " |
| 276 | —(CH$_2$)$_3$OCO—C$_6$H$_4$—Cl | " | " |
| 277 | —(CH$_2$)$_3$OCO—C$_6$H$_4$(HOOC) | " | " |

Formula (I): X = H  Y = C$_6$H$_5$—N=N—

| | | | |
|---|---|---|---|
| 278 | —(CH$_2$)$_2$OCOCH$_3$ | golden yellow | " |
| 279 | —(CH$_2$)$_2$OCOCH$_2$Cl | " | " |
| 280 | —(CH$_2$)$_2$OCOC(CH$_3$)$_3$ | " | " |
| 281 | —(CH$_2$)$_2$OCOCH$_2$CH(C$_2$H$_5$)CH$_2$CH$_2$CH$_2$CH$_3$ | | |

EXAMPLE 282

40.25 parts of the dye of Example 15, 14 parts of phenyl isocyanate and 1 part of pyridine are introduced into 300 parts of o-dichlorobenzene and heated to 150° to 160° C. The dye passes into solution. The whole is kept for four hours at 150° to 160° C. and during cooling is diluted with 50 parts of ethanol and 250 parts of cyclohexane. After standing overnight the yellow crystals are suction filtered, washed with methanol and dried. 38.9 parts of the corresponding dye (R=—CH$_2$CH$_2$C-H$_2$OCONHC$_6$H$_5$) is obtained which dyes polyester yellow shades. The dyeings have good light fastness and resistance to contact heat.

The following dyes are prepared by the same procedure:

| Example | R | Shade | Material dyed |
|---|---|---|---|
| Formula (I): X = Y = H | | | |
| 283 | —(CH$_2$)$_2$OCONHC$_6$H$_5$ | greenish yellow | polyester |
| 284 | —(CH$_2$)$_2$OCONH—C$_6$H$_4$—CH$_3$ | " | " |
| 285 | —(CH$_2$)$_2$OCONH—C$_6$H$_4$—CF$_3$ | " | " |
| 286 | —(CH$_2$)$_2$OCOHN—C$_6$H$_3$(Cl)—Cl | " | " |
| 287 | —(CH$_2$)$_3$OCONHC$_6$H$_5$ | " | " |
| 288 | —(CH$_2$)$_2$OCOHN—C$_6$H$_5$ | | |

-continued

| Example | R | Shade | Material dyed |
|---|---|---|---|
| 289 | —(CH$_2$)$_3$OCONH—C$_6$H$_4$(Cl) | " | " |
| 290 | —(CH$_2$)$_3$OCONH—C$_6$H$_3$(Cl)(OCH$_3$) | " | " |
| 291 | —(CH$_2$)$_6$OCONHC$_6$H$_5$ | " | " |
| 292 | —(CH$_2$)$_2$O(CH$_2$)$_2$OCONHC$_6$H$_5$ | " | " |
| 293 | —(CH$_2$)$_2$O(CH$_2$)$_2$OCO—C$_6$H$_4$(CH$_3$) | " | " |
| 294 | —(CH$_2$)$_2$O(CH$_2$)$_2$OCO—C$_6$H$_3$(Cl)(Cl) | " | " |

Formula (I): X = H  Y = Cl

| | | | |
|---|---|---|---|
| 295 | —(CH$_2$)$_2$OCONHC$_6$H$_5$ | yellow | " |
| 296 | —(CH$_2$)$_2$OCONH—C$_6$H$_4$(Cl) | " | " |
| 297 | —(CH$_2$)$_2$OCONH—C$_6$H$_4$(CF$_3$) | " | " |
| 298 | —(CH$_2$)$_3$OCONH—C$_6$H$_4$(CH$_3$) | " | " |
| 299 | —(CH$_2$)$_3$OCONH—C$_6$H$_4$(Cl) | " | " |
| 300 | —(CH$_2$)$_3$OCONH—C$_6$H$_3$(Cl)(Cl) | " | " |
| 301 | —(CH$_2$)$_3$OCONH—C$_6$H$_3$(Cl)(OCH$_3$) | " | " |
| 302 | —(CH$_2$)$_6$OCONH—C$_6$H$_3$(Cl)(Cl) | " | " |
| 303 | —(CH$_2$)$_2$O(CH$_2$)$_2$OCONHC$_6$H$_5$ | " | " |
| 304 | —(CH$_2$)$_2$O(CH$_2$)$_2$OCO—NH—C$_6$H$_4$(CH$_3$) | " | " |
| 305 | —(CH$_2$)$_2$O(CH$_2$)$_2$OCONH—C$_6$H$_4$(Cl) | " | " |
| 306 | —(CH$_2$)$_2$O(CH$_2$)$_2$OCONH—C$_6$H$_3$(Cl)(Cl) | " | " |

Formula (I): X = H  Y = CH$_3$

| | | | |
|---|---|---|---|
| 307 | —(CH$_2$)$_2$OCONHC$_6$H$_5$ | reddish yellow | " |
| 308 | —(CH$_2$)$_2$OCONH—C$_6$H$_4$(Cl) | " | " |
| 309 | —(CH$_2$)$_3$OCONHC$_6$H$_5$ | " | " |
| 310 | —(CH$_2$)$_3$OCONH—C$_6$H$_3$(Cl)(Cl) | " | " |
| 311 | —(CH$_2$)$_2$O(CH$_2$)$_2$OCONHC$_6$H$_5$ | " | " |

EXAMPLE 312

A mixture of 300 parts of chlorobenzene, 35.4 parts of the dye from Example 1 and 30 parts of phosphorus oxychloride is boiled under reflux for four hours. The dye passes into solution. The whole is filtered while hot and 20 parts of methanol is added to the filtrate during cooling of the same. The whole is then allowed to stand overnight, and the dye which has separated in crystalline form is suction filtered, washed with methanol and dried. 28 parts of dye (R=—$CH_2CH_2Cl$) having a chlorine content of 8.8% (calculated 9.5%) is obtained. The dye goes onto fibers and cloth of polyesters from an aqueous liquor in greenish yellow shades. The dyeings have good fastness to light and dry-heat pleating and setting.

EXAMPLE 313

The phosphorus oxychloride in Example 312 is replaced by an equivalent amount of phosphorus tribromide. 36 parts of dye (R=$CH_2CH_2Br$) is obtained having a bromine content of 17.5% (calculated 19.2%); it has similar tinctorial properties.

The dyes in the following Table are prepared analogously:

| Example | R | Shade | Material dyed |
|---|---|---|---|
| Formula (I): X = Y = H | | | |
| 314 | —$CH_2CH_2CH_2Cl$ | greenish yellow | polyester |
| 315 | —$CH_2CH_2CH_2Br$ | " | " |
| 316 | —$CH_2CH_2OCH_2CH_2Br$ | " | " |
| Formula (I): X = H Y = Cl | | | |
| 317 | —$CH_2CH_2Cl$ | yellow | " |
| 318 | —$CH_2CH_2Br$ | " | " |
| 319 | —$CH_2CH_2CH_2Cl$ | " | " |
| 320 | —$CH_2CH_2CH_2Br$ | " | " |
| 321 | —$CH_2CH_2OCH_2CH_2Br$ | " | " |

EXAMPLE 322

36.8 parts of the dye of Example 6 is boiled in 200 parts of acetic anhydride for four hours under reflux. After cooling, the product is suction filtered, washed with acetone and dried. 36.2 parts of the corresponding mixed anhydride is obtained (R=—$CH_2COOCOCH_3$).

20.5 parts of the anhydride thus obtained is introduced into 150 parts of methyl glycol and boiled under reflux for two hours. After cooling, the precipitate is suction filtered, washed with methanol and dried. 20.1 parts of the corresponding dye (R=—$CH_2COOCH_2CH_2OCH_3$) is obtained; it dyes polyester fibers and cloth greenish yellow shades having good fastness to light and dry-heat pleating and setting.

EXAMPLE 323

20.5 parts of the anhydride obtained according to Example 322 is introduced into a mixture of 100 parts of dimethylformamide and 10 parts of 3-methoxy-propylamine and stirred for two hours at 120° C. The whole is then diluted with 50 parts of 50% aqueous methanol, allowed to cool, suction filtered and dried. 22.1 parts of the dye having the formula of Example 1 with R=—$CH_2CONHCH_2CH_2CH_2OCH_3$ is obtained which is identical both chemically and tinctorially with the dye described in Example 7.

The following dyes are obtained analogously with Examples 322 and 323:

| Example | R | Shade | Material dyed |
|---|---|---|---|
| Formula (I): X = Y = H | | | |
| 324 | —$CH_2COO(CH_2)_5OH$ | greenish yellow | polyester |
| 325 | —$CH_2COOCH_2\overset{\underset{\displaystyle C_2H_5}{\mid}}{C}HCH_2CH_2CH_2CH_3$ | " | " |
| 326 | —$CH_2CONHC_4H_9$ | " | " |
| 327 | —$CH_2CONHCH_2CH_2OH$ | " | " |
| 328 | —$CH_2CONH(CH_2)_5CN$ | " | " |
| 329 | —$CH_2CONH(CH_2)_3N\begin{pmatrix}O\\\parallel\\\end{pmatrix}$ | " | " |
| 330 | —$CH_2CON(C_4H_9)_2$ | " | " |
| 331 | —$CH_2CON\begin{matrix}CH_3\\ \\CH_2CH_2OH\end{matrix}$ | " | " |
| 332 | —$CH_2CON\begin{matrix}CH_2CH_2OH\\ \\C_6H_5\end{matrix}$ | " | " |
| 333 | —$CH_2CON\bigcirc$ | " | " |
| Formula (I): X = H Y = Cl | | | |
| 334 | —$CH_2COOCH_2CH_2OH$ | yellow | " |
| 335 | —$CH_2COOCH_2\overset{\underset{\displaystyle C_2H_5}{\mid}}{C}HCH_2CH_2CH_2CH_3$ | " | " |
| 336 | —$CH_2COOCH_2CH_2OCH_2CH_2OH$ | " | " |
| 337 | —$CH_2CONHCH_2CH_2CH_2OCH_2\overset{\underset{\displaystyle C_2H_5}{\mid}}{C}H(CH_2)_3CH_3$ | " | " |
| 338 | —$CH_2CONHCH_2CH_2CH_2OH$ | " | " |

-continued

| Example | R | Shade | Material dyed |
|---------|---|-------|---------------|
| 339 | —CH$_2$CONHCH$_2$CHOHCH$_3$ | " | " |
| 340 | —CH$_2$CONH(CH$_2$)$_6$CN | " | " |
| 341 | —CH$_2$CONH(CH$_2$)$_6$N◁ | " | " |
| 342 | —CH$_2$CON(CH$_3$)(CH$_2$CH$_2$OH) | " | " |
| 343 | —CH$_2$CON(CH$_2$CH$_2$OH)$_2$ | " | " |
| 344 | —CH$_2$CON◁ | " | " |

The following dyes are prepared analogously to Example 15:

| Example | R | Shade | Material dyed |
|---------|---|-------|---------------|
| Formula (I): X = H Y = Cl | | | |
| 345 | (CH$_2$)$_3$COOH | yellow | polyester |
| 346 | (CH$_2$)$_3$COOCH$_3$ | " | " |
| 347 | (CH$_2$)$_3$CONHC$_6$H$_5$ | " | " |
| 348 | (CH$_2$)$_5$COOH | " | " |
| 349 | (CH$_2$)$_5$COOC$_2$H$_5$ | " | " |
| 350 | (CH$_2$)$_5$CONHC$_6$H$_5$ | " | " |
| 351 | C$_2$H$_4$SC$_2$H$_4$OH | " | " |
| 352 | C$_2$H$_5$SC$_2$H$_4$OCOC$_6$H$_5$ | " | " |
| 353 | C$_2$H$_4$SC$_2$H$_4$OCOC$_2$H$_5$ | " | " |
| 354 | C$_2$H$_4$SC$_2$H$_4$OCONHC$_6$H$_5$ | " | " |

I claim:

1. An azo dye of the formula:

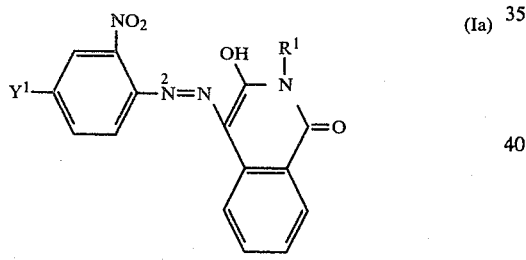

in which

Y$^1$ is hydrogen, chlorine, carboalkoxy selected from the group consisting of carbomethoxy, carboethoxy, carbopropoxy, carbobutoxy, carbo-β-ethylhexoxy, carbo-β-hydroxyethoxy, carbo-ω-hydroxypentoxy, carbo-ω-hydroxyhexoxy, carbo-β-methoxyethoxy and carbo-β-butoxyethoxy or N-substituted carbamoyl selected from the group consisting of N-methylcarbamoyl, N-ethylcarbamoyl, N-propylcarbamoyl, N-butylcarbamoyl, N-β-ethylhexylcarbamoyl, N-β-hydroxyethylcarbamoyl, N-β-hydroxypropylcarbamoyl, N-γhydroxypropylcarbamoyl, N-β-methoxyethylcarbamoyl, N-γ-methoxypropylcarbamoyl, N-γ-butoxypropylcarbamoyl, N-γ-(β'-ethylhexoxy)-propylcarbamoyl, N,N-dimethylcarbamoyl, N,N-diethylcarbamoyl, N,N-dipropylcarbamoyl, N,N-dibutylcarbamoyl, N-methyl-N-β-hydroxyethylcarbamoyl, N,N-di-β-hydroxyethylcarbamoyl, N-benzylcarbamoyl, and N-phenylethylcarbamoyl; and R$^1$ is selected from the group consisting of methyl, ethyl, propyl, isopropyl, butyl, isobutyl, tert-butyl, n-hexyl, β-ethylhexyl, n-decyl, β-methylnonyl, stearyl, β-hydroxyethyl, β-methoxyethyl, γ-hydroxypropyl, β-hydroxypropyl, γ-methoxypropyl, γ-ethoxypropyl, γ-(β-ethylhexoxy)-propyl, γ-acetoxypropyl, γ-propionyloxypropyl, benzoyloxyethyl, benzoyloxypropyl, methoxyacetoxypropyl, α-methyl-β-hydroxypropyl, β-methyl-β-hydroxypentyl, ω-hydroxyhexyl, carboxymethyl or carboxypropyl, ethoxycarbonylmethyl, methoxycarbonylpropyl, dimethylaminocarbonylmethyl, butylaminocarbonylmethyl, phenylaminocarbonylpropyl, carboxyethyl, carboxypentyl, methoxycarbonylethyl, ethoxycarbonylpentyl, diethylaminocarbonylethyl, β-ethylhexylaminocarbonylethyl, phenylaminocarbonylpentyl, acetylaminoethyl, propionylaminoethyl, acetylaminopropyl, acetylaminobutyl, propionylaminobutyl, benzoylaminobutyl, acetylaminohexyl, ω-cyanopentyl, ω-cyanohexyl, β-(β'-hydroxyethoxy)-ethyl, β-(β'-acyloxyethoxy)-ethyl and the radicals having the formulae:
—C$_2$H$_4$S—C$_2$H$_4$OH, —C$_2$H$_4$S—C$_2$H$_4$OCOC$_6$H$_5$, —C$_2$H$_4$SC$_2$H$_4$OCOC$_2$H$_5$,

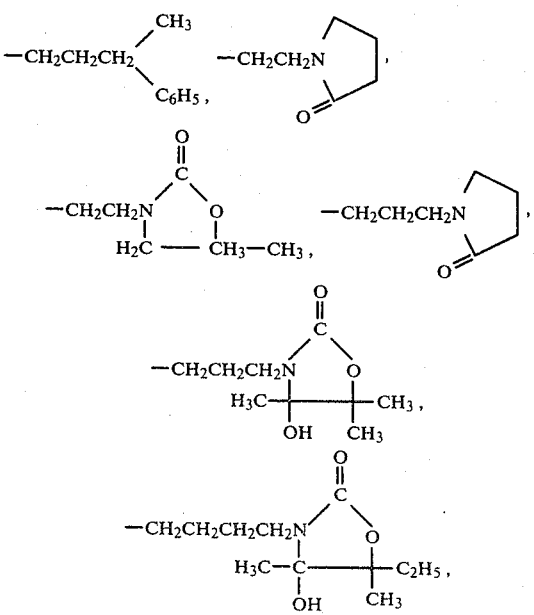

-continued
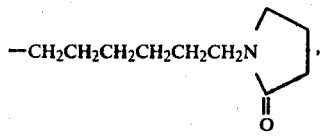
-continued
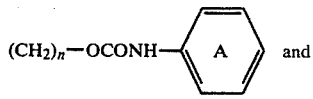 and
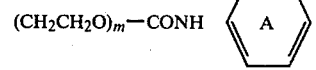
* * * * *

UNITED STATES PATENT AND TRADEMARK OFFICE
CERTIFICATE OF CORRECTION

PATENT NO. : 4,315,855
DATED      : February 16, 1982
INVENTOR(S) : E. Schefczik It is certified that error appears in the above—identified patent and that said Letters Patent is hereby corrected as shown below:

IN THE CLAIMS

In claim 1, column 32, line 55, change the formula

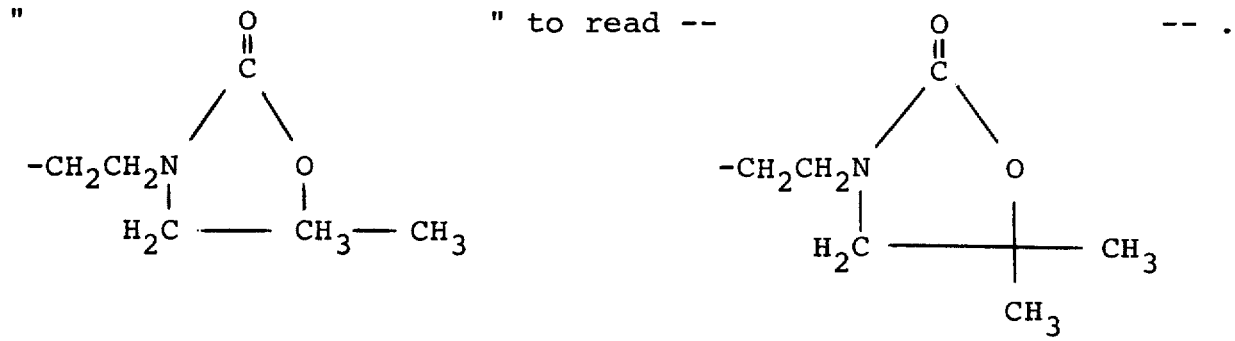

Signed and Sealed this

Sixth Day of July 1982

[SEAL]

Attest:

Attesting Officer

GERALD J. MOSSINGHOFF

Commissioner of Patents and Trademarks